US010060841B2

United States Patent
Bell et al.

(10) Patent No.: US 10,060,841 B2
(45) Date of Patent: Aug. 28, 2018

(54) FLUID DENSITOMETER

(71) Applicants: Joel David Bell, Katy, TX (US); Randall W. Dear, Humble, TX (US); David A. Tinker, Houston, TX (US)

(72) Inventors: Joel David Bell, Katy, TX (US); Randall W. Dear, Humble, TX (US); David A. Tinker, Houston, TX (US)

(*) Notice: Subject to any disclaimer, the term of this patent is extended or adjusted under 35 U.S.C. 154(b) by 94 days.

(21) Appl. No.: 15/237,010

(22) Filed: Aug. 15, 2016

(65) Prior Publication Data

US 2017/0052098 A1 Feb. 23, 2017

Related U.S. Application Data

(60) Provisional application No. 62/206,691, filed on Aug. 18, 2015.

(51) Int. Cl.
*G01N 9/00* (2006.01)
*G01N 29/036* (2006.01)

(52) U.S. Cl.
CPC ........... *G01N 9/002* (2013.01); *G01N 29/036* (2013.01); *G01N 2009/006* (2013.01); *G01N 2291/014* (2013.01); *G01N 2291/02818* (2013.01)

(58) Field of Classification Search
None
See application file for complete search history.

(56) References Cited

U.S. PATENT DOCUMENTS

| 3,516,283 | A | * | 6/1970 | Abbotts | G01N 9/002 73/24.05 |
|---|---|---|---|---|---|
| 6,029,501 | A | * | 2/2000 | Nishino | G01N 9/002 73/32 A |
| 8,166,801 | B2 | | 5/2012 | Sinha | |
| 2015/0219540 | A1 | * | 8/2015 | Casey | G01N 9/002 73/24.05 |

* cited by examiner

*Primary Examiner* — Paul West
*Assistant Examiner* — Mark A Shabman
(74) *Attorney, Agent, or Firm* — Shawn Hunter

(57) ABSTRACT

A fluid densitometer for measuring the density of fluid includes an inner tube and outer tube. A sensor assembly passes through the outer tube to contact an outer radial surface of the inner tube. The inner tube is vibrated at a predetermined frequency, and detected resonance signals are used to determine fluid density.

15 Claims, 5 Drawing Sheets

FLUID DENSITOMETER

BACKGROUND OF THE INVENTION

1. Field of the Invention

The invention relates generally to devices and methods for measuring the density of a flowing fluid.

2. Description of the Related Art

There are numerous industrial processes which involve the transport of liquids or other fluids and in which it may be desirable to measure or monitor the density of fluid being transported. Conventional densitometers used in the petrochemical industry are slip stream devices that are mounted on the exterior of a pipeline and which must divert a portion of the fluid within the pipeline outside of the pipeline in order to measure its density.

SUMMARY OF THE INVENTION

The invention provides systems and methods for measuring the density of fluid flowing through a pipe. Exemplary density measurement devices, or densitometers, are described which can be incorporated into a pipeline or other fluid flowpath so as to provide in-line fluid density measurement capability. In described embodiments, densitometers are modular devices which include a radially inner flow tube and an outer flow tube. The inner and outer flow tube are retained in a generally coaxial configuration by axial end assemblies. During operation, fluid is flowed or flows through the outer flow tube and flow occurs both radially within and outside of the inner flow tube. This permits the inner flow tube, within which fluid density is measured, to be both pressure-balanced and temperature-balanced during operation. Thus, the densitometer or densitometers provide for flow density measurement of greater accuracy.

A density sensor extends through the outer flow tube, filter media and inner flow tube in order to measure the density of fluid flowing through the inner flow tube. In preferred embodiments, a porous filter medium, such as a screen or screens, protects the outer radial surface of the inner flow tube and the density sensor from contact by debris within the fluid. In a first described embodiment, a tubular screen radially surrounds the inner flow tube. The probe conductor passes through the screen and is protected from debris outside of the screen with a protective sleeve. In an alternative embodiment, a filter screen insert is disposed into one or more of the end assemblies to filter debris from flowing radially outside of the inner flow tube.

BRIEF DESCRIPTION OF THE DRAWINGS

For a thorough understanding of the present invention, reference is made to the following detailed description of the preferred embodiments, taken in conjunction with the accompanying drawings, wherein like reference numerals designate like or similar elements throughout the several figures of the drawings and wherein.

DETAILED DESCRIPTION OF THE PREFERRED EMBODIMENTS

Figure 1:
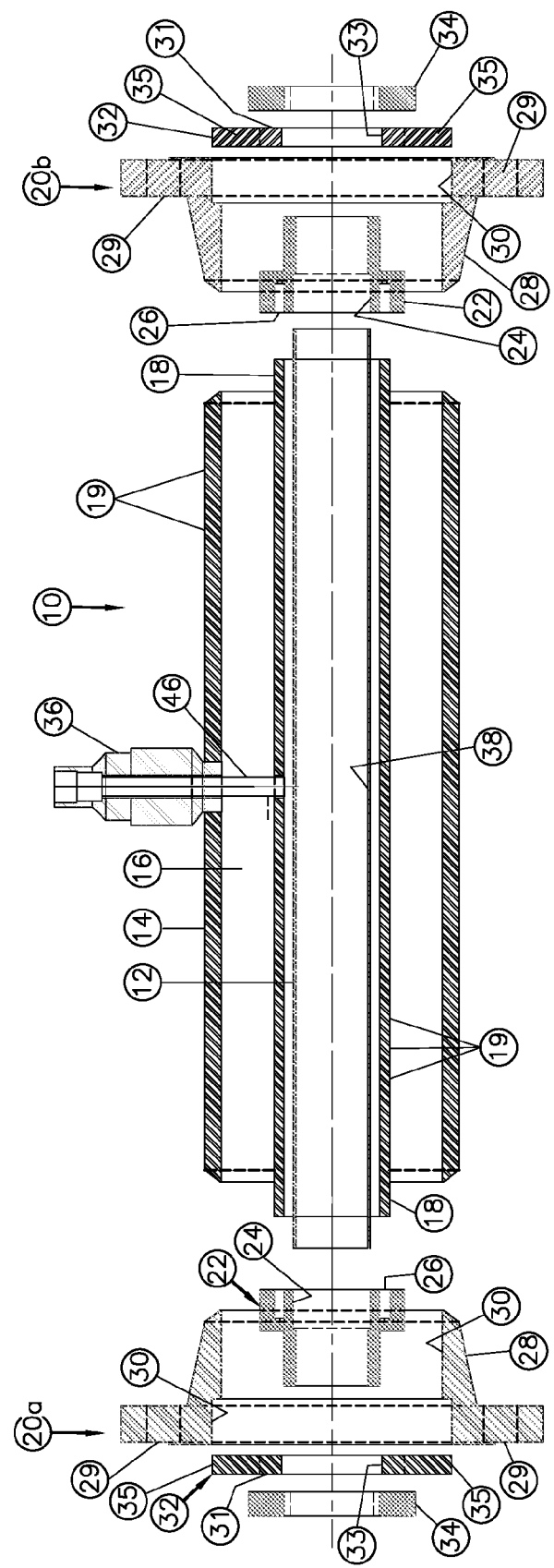
FIG. 1 is a side, cross-sectional exploded view of an exemplary fluid densitometer apparatus constructed in accordance with the present invention.

FIG. 1 depicts a first exemplary fluid densitometer 10 constructed in accordance with the present invention. The densitometer 10 includes an inner flow tube 12. An outer flow tube 14 radially surrounds the inner flow tube 12 and is generally coaxial with the inner flow tube 12. It is noted that the inner and outer flow tubes 12, 14 may each be of various sizes, from small to large, however, the outer flow tube 14 will always be radially larger than the inner flow tube 12 so as to define an intermediate flow space 16 radially between the inner and outer flow tubes 12, 14. Preferably, the inner and outer flow tubes 12, 14 each have substantially uniform diameter along their lengths. Although the inner and outer flow tubes 12, may be of any length, it is currently preferred that their lengths be from about 12 inches to about 36 inches.

A cylindrical screen 18 radially surrounds the inner flow tube 12 and contains perforations or openings which permit fluid to pass while blocking passage of certain solid materials therethrough. In preferred embodiments, the screen 18 is a sand screen or other screen, of a type known in the art for capturing fines and small debris and having flow openings, depicted schematically at 19. According to currently preferred embodiments, the screen 18 blocks passage of solids larger than about 40 microns as fluid within the flow space 16 passes through the screen 18 from its radial exterior inwardly toward the inner flow tube 12. However, other types of screens can also be used as the filter medium 18. Also, while a 40 micron filter is preferred, other filter sizes can be used, depending upon the nature of the fluid being flowed and the size of the debris or solids within the fluid.

Axial end assemblies, generally indicated at 20*a* and 20*b*, securely retain the inner and outer flow tubes 12, 14 and the screen 18 in generally coaxial, spaced relation with respect to each other. In addition, the axial end assemblies 20 permit fluid flow into and out of the flow tubes 12, 14 so that fluid density can be measured. The axial end assemblies 20 also permit the densitometer assembly 10 to be incorporated into a pipeline or other flow path. In the depicted embodiment, each axial end assembly 20 includes a tube holder 22 having a central recess 24 for retaining the inner flow tube 12 and a surrounding outer recess 26 for retaining the filter medium 18.

Figure 2:
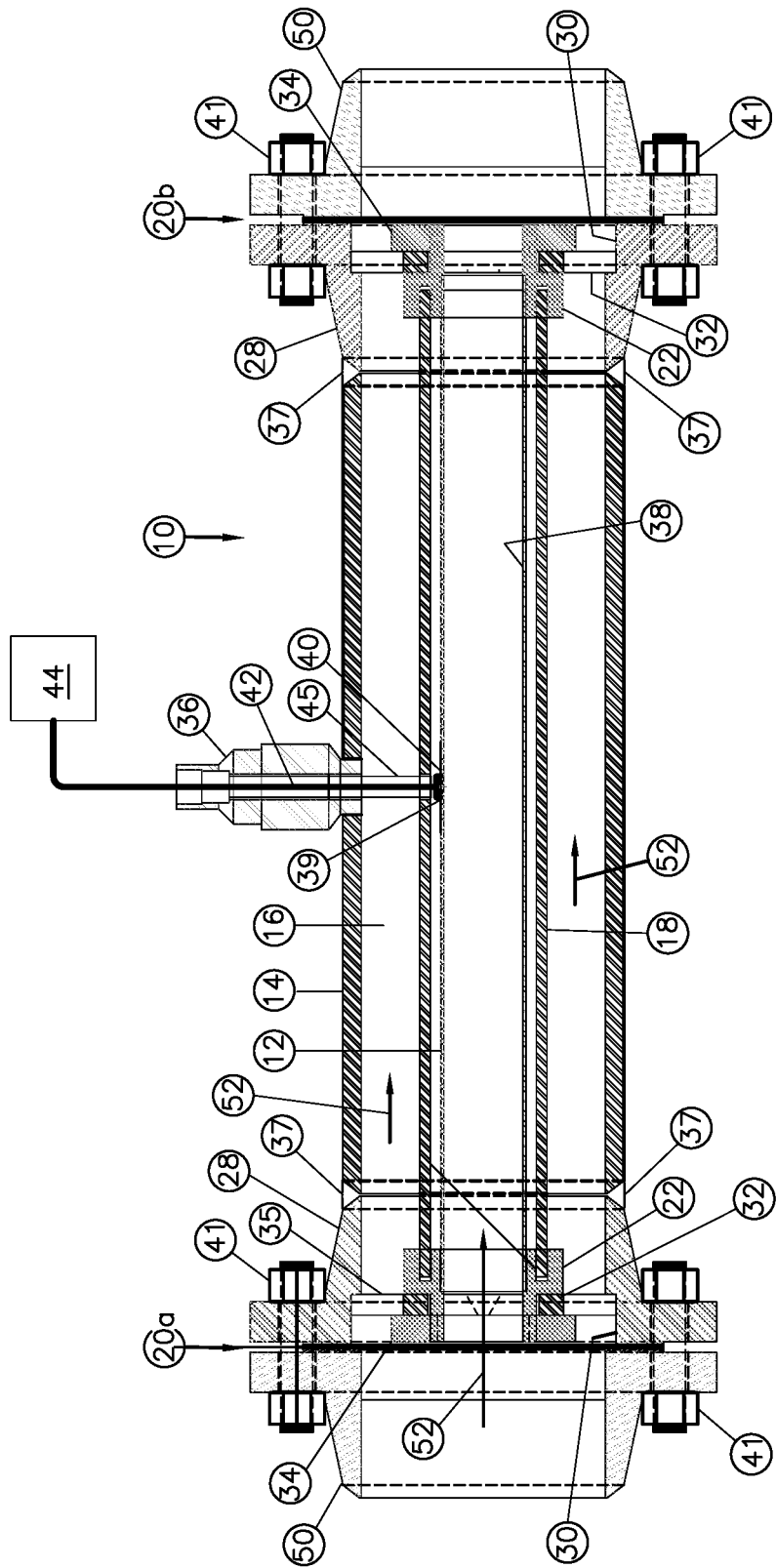
FIG. 2 is a side, cross-sectional view of the fluid densitometer apparatus of FIG. 1, now assembled as an in-line densitometer.
Figure 3:
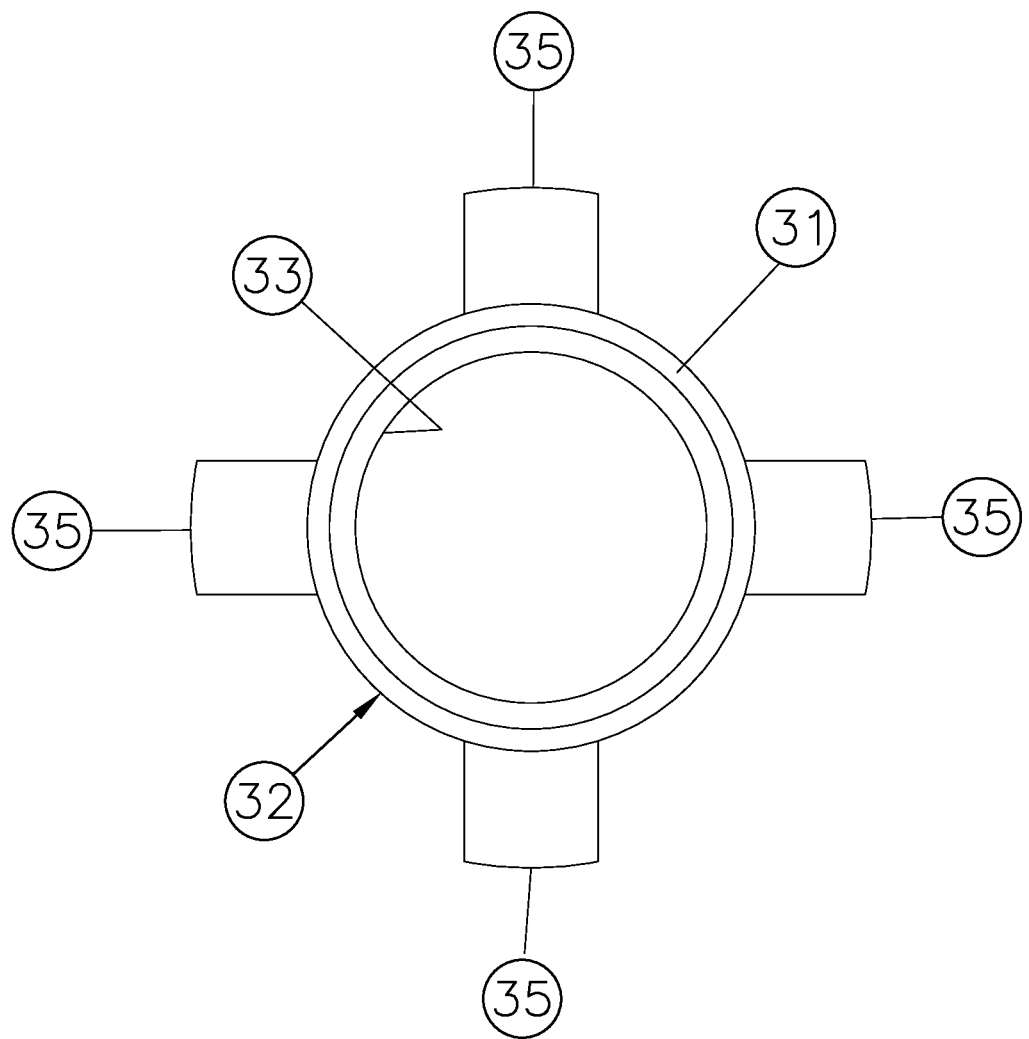
FIG. 3 is an isometric view of an exemplary stator used with the densitometer of FIG. 1.

Each axial end assembly 20 (20*a*, 20*b*) also includes a process connection 28. The process connection 28 is a generally cylindrical member having an expanded diameter orifice 30 formed within. Stator 32 and securing nut 34 secure the tube holder 22 to the process connection 28. The process connection 28 is shaped and sized to allow interconnection of the densitometer apparatus 10 into a pipeline or other flow path. For example, the outer radial portions of the process connection 28 might be perforated with openings 29 through which bolts or other connectors (41 in FIG. 2) can be disposed. An exemplary stator 32 is shown apart from the other components of the densitometer apparatus 10. The stator 32 has a ring 31 with central opening 33. Arms 35 extend radially outwardly from the ring 31. When the densitometer apparatus 10 is assembled, as shown in FIG. 2, the arms 35 will reside within the opening 30 of the process connection 28 which is effective to centralize the inner flow tube 12 and screen 18 with respect to the outer flow tube 14. When the densitometer apparatus 10 is assembled, as shown in FIG. 2, the process connections 28 are affixed to the outer tube 14 by welds 37. FIG. 2 also illustrates the densitometer 10 having been incorporated into a pipeline which includes piping members 50. Fluid is flowed through the densitometer 10, as indicated by arrows 52. It can be seen that the fluid flows both radially within the inner flow tube 12 and radially outside of the inner flow tube 12.

A sensor assembly 36 is disposed through the radial side of the densitometer apparatus 10 in order to detect the density of fluid flowing through the flowbore 38 of the inner flow tube 12. In preferred embodiments, the sensor assembly 36 includes a means for vibrating the inner flow tube 12 by a vibratory resonant driver 39 which is mounted on the inner flow tube 12. The sensor assembly 36 also include a resonance receiver 40. The resonance receiver 40 is also mounted on the inner flow tube 12 and is adapted to detect vibrations which are initiated by the driver 39. The resonance receiver 40 should be placed apart from the driver 39 upon the outer radial surface of the inner flow tube 12. However, it is preferred that the driver 39 and receiver 40 be disposed upon the center one-third of the length of the inner flow tube 12. Preferably, the resonant frequency of the inner flow tube 12 is calibrated on three different densities prior to installation in a pipeline or flowing stream.

The sensor assembly 36 also preferably includes flexible conductive wiring 42 which extends through the outer flow tube 14 and the screen 18 in order to electrically interconnect the resonant driver 39 and the resonance receiver 40 with a controller 44. The controller 44 is preferably a programmable logic controller which is operable to vibrate the driver 39 at predetermined frequencies. The controller 44 is also operable to receive detected resonance signals from the resonance receiver 40. Signals received from the resonance receiver 40 are then used to determine the density of fluid flowing m within the flowbore 38 of the inner flow tube 12. The signal is translated to the resonant frequency which is proportional to the density of fluid. A suitable controller for use as the controller 44 would be a Model 003 processor which is available commercially from Analytical Measurements of Hopatcong, N.J.

A protective tube 46 radially surrounds the conductive wiring 42 as the wiring 42 passes in between the outer flow tube 14 and the screen 18. The protective tube 46 prevents any debris which might be present in fluid flowing radially outside of the screen 18 from damaging the wiring 42. The protective tube 46 is preferably formed of a non-conductive material, such as plastic or ceramic, so that the wiring 42 is dielectrically isolated from conductive materials. Preferably also, a non-conductive coating is resonant driver 39 and resonance receiver 40 to dielectrically isolate the wiring connection and components mounted on the inner flow tube 12.

In operation, fluid flows into the axial end assembly 20a and into both the flowbore 38 of the inner flow tube 12 and the intermediate flow space 16 defined between the inner and outer flow tubes 12, 14. As fluid flows through the inner flow tube 12, the fluid density is detected. In the depicted embodiment, fluid flows from the first axial end assembly 20a toward the second axial end assembly 20b in the direction of flow arrows 52. It is noted, however, that flow through the densitometer 10 can be bi-directional. Fluid within the intermediate flow space 16 can pass through the screen 18 via the openings 19 and subject the outer radial surface of the inner flow tube 12 to fluid pressure that is equivalent to the fluid pressure within the inner flow tube 12. The inventors believe that, by pressure-balancing the inner flow tube 12 in this manner, fluid density readings are more accurate. Fluid pressure within the flowbore 38 of the inner flow tube 12 is balanced by fluid pressure within the intermediate flow space 16 outside of the inner flow tube 12. In particular embodiments, the controller 44 is mounted on the outside of the densitometer 10 and is driven by 24 volts dc. The voltage is used to excite the driver 39 mounted to the outside of the inner flow tube 12. The resonance receiver 40 provides the frequencies to the controller 44 which are translated to the resonant frequency, which is proportional to the density of fluid within the inner flow tube 12.

Figure 4:
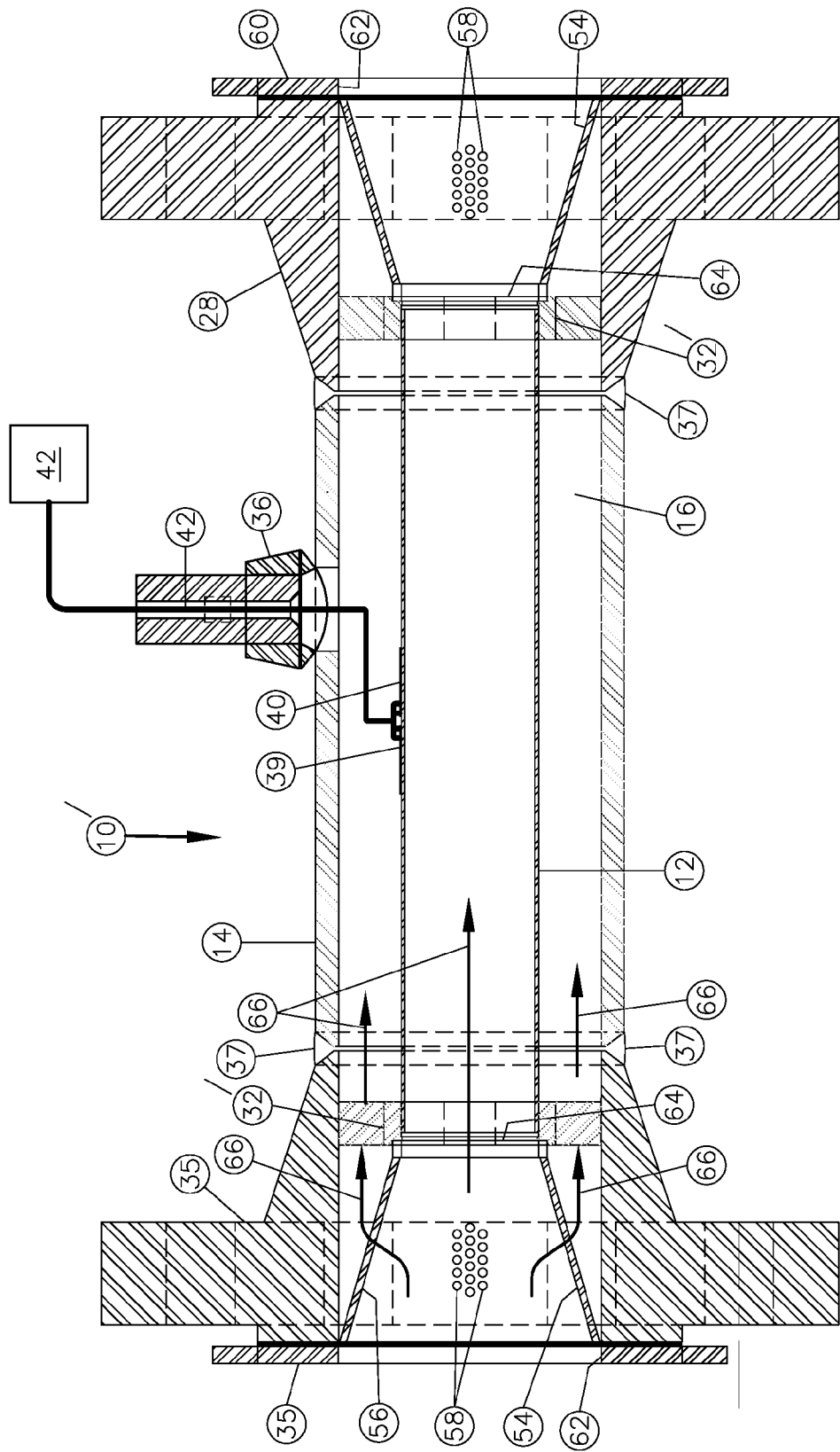
FIG. 4 is a side, cross-sectional view of an alternative embodiment for a fluid densitometer constructed in accordance with the present invention.
Figure 5:
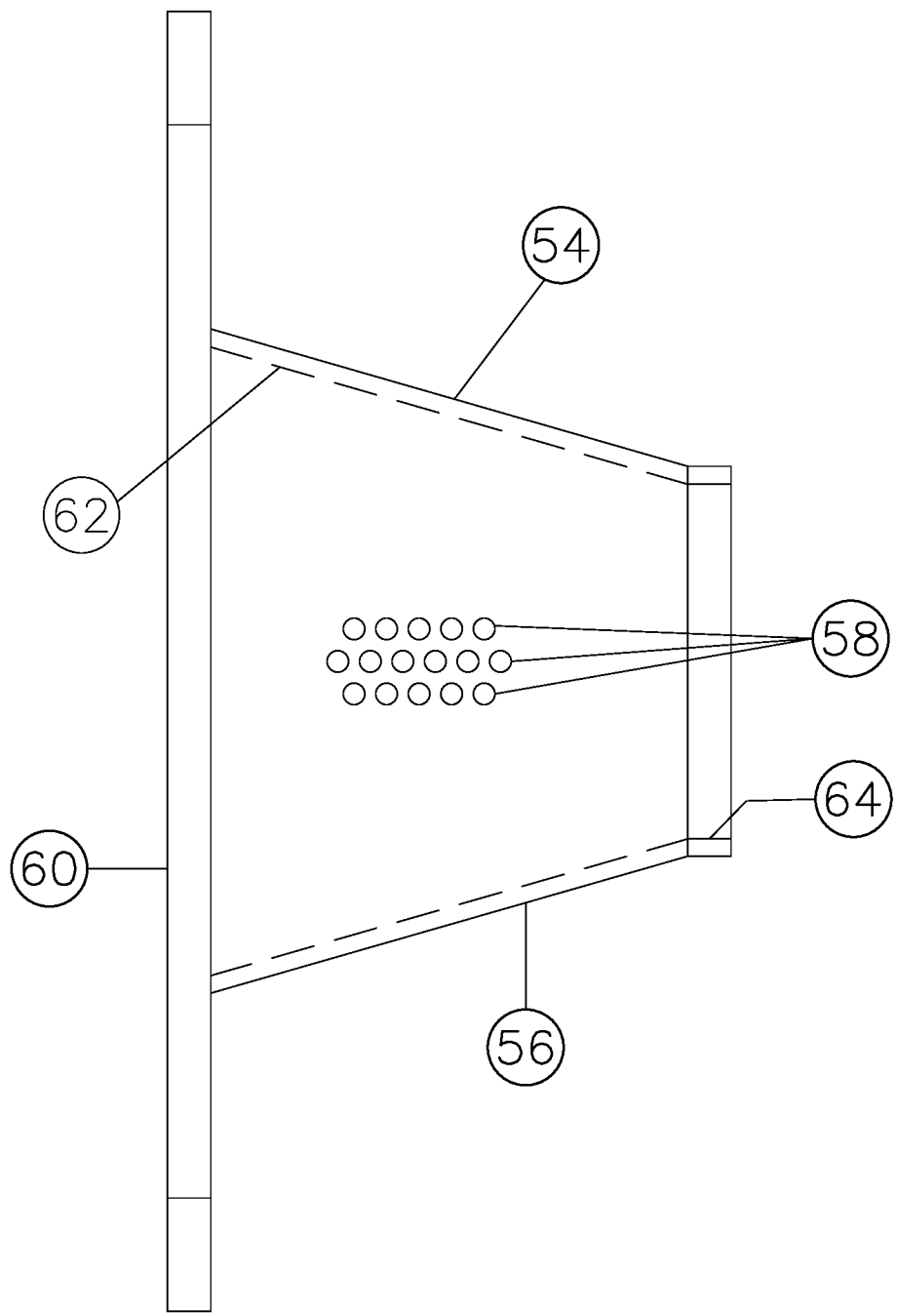
FIG. 5 is a side view of an exemplary screen insert used in the fluid densitometer of FIG. 4.

FIG. 4 illustrates an alternative densitometer 10'. Except where described otherwise, the densitometer 10' is constructed and operates in the same manner as the densitometer 10 described previously. Inner flow tube 12 resides radially within the outer flow tube 14. Preferably, the inner flow tube 12 is maintained in a generally coaxial relation with the outer flow tube 14 by a pair of stator elements 32'. At least one screening insert 54 is disposed within a process connection 28. In the embodiment depicted in FIG. 4, there are two screening inserts 54. However, there may be only a single screening insert 54 at one axial end of the densitometer 10'. An exemplary screening insert 54 is illustrated in FIG. 5 and includes a generally conical screening portion 56 with fluid flow openings 58 and a base plate 60. The screening insert 54 presents an upstream opening 62 and a downstream opening 64. When the screening insert 54 is inserted into its surrounding process connection 28, the downstream opening 64 mates with the inner flow tube 12.

During operation, fluid is flowed in the direction indicated by arrows 66. Unfiltered fluid flows through the inner flow tube 12. Fluid which flows between the inner flow tube 12 and outer flow tube 14 must pass through the screening insert 54, thereby removing debris solids from the fluid. Removal of debris will protect the resonant driver 39, resonance receiver 40 and wiring 42. The densitometer apparatus 10' allows pressure balanced density detection because fluid will flow on the outside of the inner flow tube 12 as well as the inside of the inner flow tube 12.

Those of skill in the art will recognize that numerous modifications and changes may be made to the exemplary designs and embodiments described herein and that the invention is limited only by the claims that follow and any equivalents thereof.

What is claimed is:

1. A fluid densitometer comprising:
an inner flow tube;
an outer flow tube that lies radially outside of the inner flow tube;
the inner and outer flow tubes being associated with a flow of fluid to flow fluid within the inner flow tube and between the inner flow tube and the outer flow tube to pressure-balance the inner flow tube; and
a sensor assembly to detect a resonant frequency of the inner flow tube, the sensor assembly being disposed through the outer flow tube to reside within a space defined radially between the inner and outer flow tubes.

2. The fluid densitometer of claim 1 further comprising a screen to remove debris from fluid flowing between the inner flow tube and the outer flow tube to protect portions of the sensor assembly from damage by debris.

3. The fluid densitometer of claim 2 wherein the screen further comprises a cylindrical screen which resides radially between the outer flow tube and the inner flow tube.

4. The fluid densitometer of claim 2 wherein the screen further comprises a screening insert having a generally conical screening portion which mates with the inner flow tube and filters debris within the flow of fluid from entering an intermediate flow space between the inner flow tube and the outer flow tube.

5. The fluid densitometer of claim 1 wherein the sensor assembly further comprises:
a resonant driver for vibrating the inner flow tube; and
a resonance receiver to detect resonance created by the resonant driver.

6. The fluid densitometer of claim 5 wherein the sensor assembly further comprises a controller to vibrate the resonant driver and receive a signal indicative of resonant frequency from the resonance receiver.

7. The fluid densitometer of claim 6 further comprising:
conductive wiring which extends between the resonant driver, resonance receiver and the controller for transmission of power and data to the controller; and
a protective tube which radially surrounds the conductive wiring along a portion of its length.

8. A fluid densitometer comprising:
an inner flow tube;
an outer flow tube that lies radially outside of the inner flow tube;
the inner and outer flow tubes being associated with a flow of fluid to flow fluid within the inner flow tube and between the inner flow tube and the outer flow tube to pressure-balance the inner flow tube;
a sensor assembly having a resonant sensor to detect a resonant frequency of the inner flow tube, the sensor assembly being disposed through the outer flow tube to contact an outer radial surface of the inner flow tube; and
the sensor assembly further including a controller which can determine fluid density of fluid flowing within the inner flow tube based upon the detected resonant frequency.

9. The densitometer of claim 8 wherein the sensor assembly further includes a resonant driver to vibrate the inner flow tube.

10. The densitometer of claim 9 further comprising:
conductive wiring which extends between the resonant driver, resonance receiver and the controller for transmission of power and data to the controller; and
a protective tube which radially surrounds the conductive wiring along a portion of its length.

11. The densitometer of claim 8 further comprising a screen to remove debris from fluid flowing between the inner flow tube and the outer flow tube to protect portions of the sensor assembly from damage by debris.

12. The densitometer of claim 11 wherein the screen further comprises a cylindrical screen which resides radially between the outer flow tube and the inner flow tube.

13. The densitometer of claim 11 wherein the screen further comprises a screening insert having a generally conical screening portion which mates with the inner flow tube and filters debris within the flow of fluid from entering an intermediate flow space between the inner flow tube and the outer flow tube.

14. A method of determining fluid density of a fluid within an inner flow tube of a densitometer, the method comprising the steps of:
flowing the fluid through the inner flow tube;
flowing the fluid through an intermediate flow space between the inner flow tube and an outer flow tube which radially surrounds the inner flow tube to pressure-balance the inner flow tube;
disposing a sensor assembly through the outer tube to contact an outer radial surface of the inner tube;
vibrating the inner flow tube with a resonant driver and detecting the vibrations with the sensor assembly;
determining a resonant frequency for the inner flow tube during vibration of the inner flow tube; and
determining fluid density based upon the determined resonant frequency.

15. The method of claim 14 further comprising the step of screening debris from the fluid flowing through the intermediate flow space.

\* \* \* \* \*